United States Patent [19]

Wingert et al.

[11] Patent Number: 5,500,446

[45] Date of Patent: Mar. 19, 1996

[54] FUNGICIDAL MIXTURES

[75] Inventors: Horst Wingert; Hubert Sauter, both of Mannheim; Eberhard Ammermann, Heppenheim; Gisela Lorenz, Neustadt; Reinhold Saur, Böhl-Iggelheim; Klaus Schelberger, Gönnheim; Manfred Hampel, Neustadt, all of Germany

[73] Assignee: BASF Aktiengesellschaft, Ludwigshafen, Germany

[21] Appl. No.: 305,339

[22] Filed: Sep. 15, 1994

[30] Foreign Application Priority Data

Sep. 24, 1993 [DE] Germany .................. 43 32 628.5

[51] Int. Cl.$^6$ .......................... A01N 37/18; A01N 47/10
[52] U.S. Cl. ................................ 514/483; 514/619
[58] Field of Search .................. 514/483, 619

[56] References Cited

U.S. PATENT DOCUMENTS

| | | | |
|---|---|---|---|
| 2,457,674 | 12/1948 | Heuberger | 167/22 |
| 2,504,404 | 4/1950 | Flenner | 167/22 |
| 3,248,400 | 4/1966 | Flieg et al. | 260/313 |
| 3,379,610 | 4/1968 | Lyon et al. | 514/483 |

FOREIGN PATENT DOCUMENTS 0477631  4/1992  European Pat. Off. .

*Primary Examiner*—Allen J. Robinson
*Attorney, Agent, or Firm*—Oblon, Spivak, McClelland, Maier, & Neustadt

[57] ABSTRACT

A fungicidal mixture containing a) the oxime ether carboxamide of the formula I

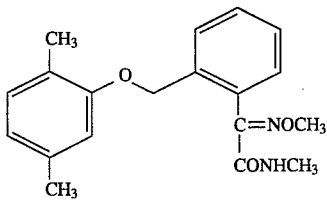

b) a dithiocarbamate (II) selected from the group

- manganese ethylenebis(dithiocarbamate) (zinc complex) (IIa),

- manganese ethylenebis(dithiocarbamate) (IIb),

- zinc ammoniate ethylenebis(dithiocarbamate) (IIc) and

- zinc ethylenebis(dithiocarbamate) (IId)

in a synergistically active amount is described.

7 Claims, No Drawings

FUNGICIDAL MIXTURES

The present invention relates to a fungicidal mixture which contains
a) the oxime ether carboxamide of the formula I

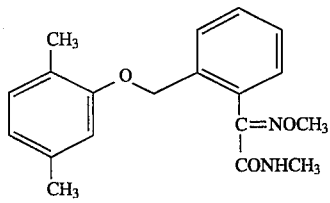

and
b) a dithiocarbamate (II) selected from the group
- manganese ethylenebis(dithiocarbamate) (zinc complex) (IIa),
- manganese ethylenebis(dithiocarbamate) (IIb),
- zinc ammoniate ethylenebis(dithiocarbamate) (IIc) and
- zinc ethylenebis(dithiocarbamate) (IId)
in a synergistically active amount.

The invention additionally relates to processes for controlling harmful fungi using mixtures of the compounds I and II and the use of the compound I and the compounds II for the production of mixtures of this type.

The compound of the formula I, its preparation and its action against harmful fungi are disclosed in the literature (EP-A 477 631).

The dithiocarbamates II (IIa: common name: mancozeb, US-A 3,379,610; IIb: common name: maneb, US-A 2,504,404; IIc: former common name: metiram, US-A 3,248,400; IId: common name: zineb, US-A 2,457,674), their preparation and their action against harmful fungi are likewise known.

With respect to a decrease in the application rates and an improvement of the spectrum of action of known compounds, the present invention is based on mixtures which, with a reduced total amount of applied active compounds, have an improved action against harmful fungi (synergistic mixtures).

Accordingly, the mixtures defined at the beginning have been found. It has additionally been found that on simultaneous joint or separate application of the compound I and the compounds II or on application of the compound I and the compounds II in succession, harmful fungi can be controlled better than with the individual compounds.

The compound of the formula I can be present in the E or the Z configuration with respect to the C=X double bond (with respect to the carboxylic acid function group). Accordingly, it can be used in the mixture according to the invention in each case either as the pure E or Z isomer or as an E/Z isomer mixture.. The E/Z isomer mixture or the E isomer is preferably used, the E isomer being particularly preferred.

Because of the basic character of the NH group, the compound I is able to form salts or adducts with inorganic or organic acids or with metal ions.

Examples of inorganic acids are hydrohalic acids such as hydrofluoric acid, hydrochloric acid, hydrobromic acid and hydriodic acid, sulfuric acid, phosphoric acid and nitric acid.

Suitable organic acids are, for example, formic acid, carbonic acid and alkanoic acids such as acetic acid, trifluoroacetic acid, trichloroacetic acid and propionic acid and also glycolic acid, thiocyanic acid, lactic acid, succinic acid, citric acid, benzoic acid, cinnamic acid, oxalic acid, alkylsulfonic acids (sulfonic acids having straight-chain or branched alkyl radicals having 1 to 20 carbon atoms), arylsulfonic acids or -disulfonic acids (aromatic radicals such as phenyl and naphthyl which carry one or two sulfonic acid groups), alkylphosphonic acids (phosphonic acids having straight-chain or branched alkyl radicals having 1 to 20 carbon atoms), arylphosphonic acids or -diphosphonic acids (aromatic radicals such as phenyl and naphthyl which carry one or two phosphoric acid radicals), the alkyl and aryl radicals being able to carry further substituents, e.g., p-toluenesulfonic acid, salicylic acid, p-aminosalicylic acid, 2-phenoxybenzoic acid, 2-acetoxybenzoic acid etc.

Suitable metal ions are in particular the ions of the elements of the second main group, in particular calcium and magnesium, of the third and fourth main group, in particular aluminum, tin and lead, as well as of the first to eighth subgroup, in particular chromium, manganese, iron, cobalt, nickel, copper, zinc and others. The metal ions of the elements of the subgroups of the fourth period are particularly preferred. The metals can in this case be present in the different valencies applicable to them.

Preferably, the pure active compounds I and II are employed in the preparation of the mixtures, to which, if required, further active compounds against harmful fungi or other pests such as insects, arachnids or nematodes, or alternatively herbicidal, or growth-regulating active compounds or fertilizers, can be admixed.

The mixtures of the compounds I and II and the simultaneous joint or separate use of the compounds I and II are distinguished by an outstanding action against a wide spectrum of phytopathogenic fungi, in particular from the Ascomycetes and Basidiomycetes class. In some cases they are systemically active and can therefore also be employed as foliar and soil fungicides.

They have particular importance for the control of a multiplicity of fungi on various crop plants such as cotton, vegetable plants (e.g., cucumbers, beans and cucurbits), barley, grass, oats, coffee, maize, fruit plants, rice, rye, soybean, grape, wheat, decorative plants, sugar cane and a multiplicity of seeds.

In particular, they are suitable for the control of the following phytopathogenic fungi: Erysiphe graminis (powdery mildew) on cereals, Erysiphe cichoracearum and Sphaerotheca fuliginea on cucurbits, Podosphaera leucotricha on apples, Puccinia species on cereals, Rhizoctonia species on cotton and lawns, Ustilago species on cereals and sugar cane, Venturia inaequalis (scab) on apples, Helminthosporium species on cereals, Septoria nodorum on wheat, Botrytis cinerea (gray mold) on strawberries and vines, Cercospora arachidicola on groundnuts, Pseudocercosporella herpotrichoides on wheat and barley, Pyricularia oryzae on rice, Phytophthora infestans on potatoes and tomatoes, Plasmopara viticola on vines, Alternaria species on vegetables and fruit and also Fusarium and Verticillium species.

They are additionally applicable in the protection of materials (e.g., wood preservation), for example against Paecilomyces variotii.

The compounds I and II can be applied simultaneously jointly or separately, or in succession, the sequence in the case of separate application in general having no effect on the control success.

The compounds I and II are customarily applied in a weight ratio of from 2000:1 to 5:1, preferably from 1000:1 to 5:1, in particular from 500:1 to 5:1 (II:I).

Depending on the type of effect desired, the application rates of the mixtures according to the invention are from 0.005 to 0.5 kg/ha, preferably from 0.01 to 0.5 kg/ha, in particular from 0.01 to 0.3 kg/ha, for the compound I. The application rates for the compounds II are correspondingly from 0.1 to 10 kg/ha, preferably from 0.5 to 5 kg/ha, in particular from 1 to 4 kg/ha.

In the treatment of seed, application rates of mixture of from 0.001 to 100 g/kg of seed, preferably from 0.01 to 50 g/kg, in particular from 0.01 to 10 g/kg, are generally used.

If harmful fungi which are pathogenic for plants are to be controlled, the separate or joint application of the compounds I and II or of the mixtures of the compounds I and II is carried out by spraying or dusting the seeds, the plants or the soil before or after sowing of the plants or before or after emergence of the plants.

The fungicidal synergistic mixtures according to the invention and the compounds I and II can be prepared, for example, in the form of directly sprayable solutions, powders and suspensions or in the form of high-percentage aqueous, oily or other suspensions, dispersions, emulsions, oil dispersions, pastes, dusting compositions, broadcasting compositions or granules and applied by spraying, atomizing, dusting, broadcasting or watering. The application form is dependent on the intended use; it should in each case guarantee a dispersion of the mixture according to the invention which is as fine and uniform as possible.

The formulations are prepared in a manner known per se, e.g., by addition of solvents and/or carriers. Inert additives such as emulsifiers or dispersants are customarily admixed to the formulations.

Suitable surface-active substances are the alkali metal, alkaline earth metal or ammonium salts of aromatic sulfonic acids, e.g., lignosulfonic acid, phenolsulfonic acid, naphthalenesulfonic acid and dibutylnaphthalenesulfonic acid, as well as of fatty acids, alkyl- and alkylarylsulfonates, alkyl-, lauryl ether and fatty alcohol sulfates, and also salts of sulfated hexa-, hepta- and octadecanols or fatty alcohol glycol ethers, condensation products of sulfonated naphthalene and its derivatives with formaldehyde, condensation products of naphthalene or of naphthalenesulfonic acids with phenol and formaldehyde, polyoxyethylene octylphenol ethers, ethoxylated isooctyl-, octyl- or nonylphenol, alkylphenol or tributylphenyl polyglycol ethers, alkylaryl polyether alcohols, isotridecyl alcohol, fatty alcohol-ethylene oxide condensates, ethoxylated castor oil, polyoxyethylene or polyoxypropylene alkyl ethers, lauryl alcohol polyglycol ether acetate, sorbitol esters, lignin-sulfite waste liquors or methylcellulose.

Powder, broadcasting and dusting compositions can be prepared by mixing or joint grinding of the compounds I or II or the mixture of the compounds I and II with a solid carrier.

Granules (e.g., coated, impregnated or homogeneous granules) are customarily prepared by binding the active compound or the active compounds to a solid carrier.

Fillers or solid carriers used are, for example, mineral earths such as silica gel, silicic acids, silicates, talc, kaolin, limestone, lime, chalk, bole, loess, clay, dolomite, diatomaceous earth, calcium and magnesium sulfate, magnesium oxide, ground plastics, and fertilizers such as ammonium sulfate, ammonium phosphate, ammonium nitrate, ureas and vegetable products such as cereal flour, tree bark meal, wood meal and nutshell meal, cellulose powder or other solid carriers.

The formulations in general contain from 0.1 to 95% by weight, preferably from 0.5 to 90% by weight, of one of the compounds I or II or the mixture of the compounds I and II. The active compounds are in this case employed in a purity of from 90% to 100%, preferably from 95% to 100% (according to NMR spectrum or HPLC).

The compounds I or II and the mixtures or the corresponding formulations are applied by treating the harmful fungi or the plants, seeds, soils, surfaces, materials or spaces to be kept free from them with a fungicidally active amount of the mixture, or of the compounds I and II in the case of separate application. Application can be carried out before or after attack by the harmful fungi.

Examples of the synergistic action of the mixtures according to the invention against harmful fungi.

It was possible to show the fungicidal action of the compound and of the mixtures by the following tests:

The active compounds were prepared separately or jointly as a 20% strength emulsion in a mixture of 70% by weight of cyclohexanone, 20% by weight of Nekanil® LN (Lutensol® AP6, wetting agent having emulsifier and dispersant action based on ethoxylated alkylphenols) and 10% by weight of Emulphor® EL (Emulan® EL, emulsifier based on ethoxylated fatty alcohols) and-accordingly diluted to the desired concentration with water.

Assessment followed determination of the attacked leaf areas in percent.-These percentage values were converted into degrees of action. The degrees of action of the active compound mixtures to be expected were determined according to the Colby formula [R.S. Colby, Weeds 15, (1967) 20–22] and compared with the degrees of action observed.

Colby formula:

$$E = x + y - xy/100$$

E is the degree of action to be expected, expressed in % of the untreated control, when using the mixture of the active compounds A and B in the concentrations a and b x is the degree of action, expressed in % of the untreated control, when using the active compound A in the concentration a y is the degree of action, expressed in % of the untreated control, when using the active compound B in the concentration b At a degree of action of 0, the attack of the treated plants corresponds to that of the untreated control plants; at a degree of action of 100 the treated plants showed no attack.

Activity against vine Peronospora

Leaves of potted vines of the variety Miller-Thurgau were sprayed with aqueous spray liquor which contained 80% of active compound and 20% emulsifier in the dry matter. In order to be able to assess the duration of action of the active compounds, the plants were placed in a greenhouse for 8 days after drying on of the spray coating. Only then were the leaves infected with a zoospore suspension of Plasmopara viticola (vine Peronospora). The vines were then first placed for 48 hours in a water vapor-saturated chamber at 24° C. and then for 5 days in a greenhouse at from 20 to 30° C. After this time, the plants were placed in the moist chamber again for 16 hours to accelerate escape from the sporangiophore.

Assessment of the extent of fungal outbreak on the bottoms of the leaves was then carried out.

| Active compound | Active compound concentration in the spray liquor in ppm | Degree of action in % of the untreated control |
| --- | --- | --- |
| Control (untreated) | — | 0 |
| I. | 31 | 93.5 |
|  | 16 | 87 |
| II. b | 310 | 48 |
|  | 160 | 35.3 |

-continued

| Active compound | Active compound concentration in the spray liquor in ppm | Degree of action in % of the untreated control |
|---|---|---|
| Mixture according to the invention | degree of action observed | degree of action calculated*) |
| I + II 31 + 310 1:10 mixture | 99 | 96 |
| I + II 16 + 160 1:10 mixture | 99 | 91 |

*)calculated by the Colby formula

From the results of the test it emerges that the degree of action observed in all mixture ratios is higher than the degree of action forecast by the Colby formula.

We claim:

1. A fungicidal mixture containing in a synergistically effective amount:

a) the oxime ether carboxamide of the formula I

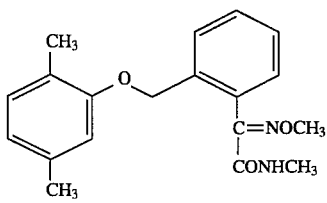

and b) a dithiocarbamate (II) selected from the group consisting of

- manganese ethylenebis(dithiocarbamate) (zinc complex) (IIa),
- manganese ethylenebis(dithiocarbamate) (IIb)
- zinc ammoniate ethylenebis(dithiocarbamate) (IIc) and
- zinc ethylenebis(dithiocarbamate) (IId), wherein the weight ratio of the compound II to the compound I is about 10:1.

2. The fungicidal mixture as claimed in claim 1, containing the oxime ether carboxamide of the formula I and manganese ethylenebis(dithiocarbamate) (zinc complex) (IIa).

3. The fungicidal mixture as claimed in claim 1, containing the oxime ether carboxamide of the formula I and manganese ethylenebis(dithiocarbamate) (IIb).

4. The fungicidal mixture as claimed in claim 1, containing the oxime ether carboxamide of the formula I and zinc ammoniate ethylenebis(dithiocarbamate) (IIc).

5. The fungicidal mixture as claimed in claim 1, containing the oxime ether carboxamide of the formula I and zinc ethylenebis(dithiocarbamate) (IId).

6. A process for controlling harmful fungi, which comprises treating the harmful fungi, their environment or the plants, seeds, soils, surfaces, materials or spaces to be kept free from them with a synergistic fungicidally effective amount of the composition of claim 1 whereby from 0.005 to 0.5 kg/ha of the compound of the formula I as claimed in claim 1 and from 0.1 to 10 kg/ha of the compound of the formula II as claimed in claim 1 are applied.

7. The process as claimed in claim 6, wherein the compound I and the compound II are applied simultaneously jointly or separately, or in succession.

* * * * *